United States Patent
Terychnyi et al.

(10) Patent No.: US 8,645,069 B2
(45) Date of Patent: Feb. 4, 2014

(54) METHOD FOR DETERMINING A STEAM DRYNESS FACTOR

(75) Inventors: Vladimir Vasilievich Terychnyi, Edmonton (CA); Marat Tokhtarovich Nukhaev, Triotsk (RU)

(73) Assignee: Schlumberger Technology Corporation, Sugar Land, TX (US)

( * ) Notice: Subject to any disclaimer, the term of this patent is extended or adjusted under 35 U.S.C. 154(b) by 472 days.

(21) Appl. No.: 12/295,315

(22) PCT Filed: Mar. 15, 2007

(86) PCT No.: PCT/RU2007/000125
§ 371 (c)(1),
(2), (4) Date: Apr. 13, 2009

(87) PCT Pub. No.: WO2007/111533

PCT Pub. Date: Oct. 4, 2007

(65) Prior Publication Data

US 2009/0248306 A1    Oct. 1, 2009

(30) Foreign Application Priority Data

Mar. 24, 2006    (RU) ............................... 2006109273

(51) Int. Cl.
*G01V 9/00*    (2006.01)
*E21B 47/06*    (2012.01)
*E21B 21/14*    (2006.01)

(52) U.S. Cl.
USPC ............... 702/12; 702/6; 702/11; 73/152.31; 73/152.39; 166/250.06

(58) Field of Classification Search
USPC ......... 702/6, 11, 12; 73/30.03, 152.3, 152.39; 166/250.06
See application file for complete search history.

(56) References Cited

U.S. PATENT DOCUMENTS

| | | | | |
|---|---|---|---|---|
| 3,782,470 A | * | 1/1974 | West et al. | 166/303 |
| 3,908,762 A | * | 9/1975 | Redford | 166/402 |
| 4,099,568 A | * | 7/1978 | Allen | 166/269 |
| 4,409,825 A | | 10/1983 | Martin et al. | |
| 4,542,993 A | | 9/1985 | Mims et al. | |
| 4,547,078 A | | 10/1985 | Long et al. | |
| 4,581,926 A | * | 4/1986 | Moore et al. | 73/152.39 |
| 4,658,208 A | | 4/1987 | Lee et al. | |
| 4,712,006 A | | 12/1987 | Zemel et al. | |
| 4,788,848 A | | 12/1988 | Hsueh | |

(Continued)

FOREIGN PATENT DOCUMENTS

| | | |
|---|---|---|
| RU | 1046665 A1 | 10/1983 |
| RU | 2046328 C1 | 10/1995 |

OTHER PUBLICATIONS

Willhite, "Thermal Operations: Over-all Heat Transfer Coefficients in Steam and Hot Water Injection Wells," Journal of Petroleum Technology, May 1967: pp. 607-615.

*Primary Examiner* — Alexander H Taningco
*Assistant Examiner* — L. Anderson

(57) ABSTRACT

A simple, applicable in the field, and extra-equipment free method is provided for determining steam dryness directly in a thermal recovery of high-viscosity oil. A non-condensable gas is added into a saturated steam being injected into a well. The presence of non-condensable gas changes partial steam pressure. Correspondingly the steam condensation temperature also changes. The borehole temperature or pressure measurements can be used to evaluate the steam dryness.

5 Claims, 1 Drawing Sheet

(56) References Cited

U.S. PATENT DOCUMENTS 4,982,786 A * 1/1991 Jennings, Jr. ............... 166/50
5,182,939 A 2/1993 Chien et al.
5,214,956 A 6/1993 Chien
5,470,749 A 11/1995 Djabbarah et al.

* cited by examiner

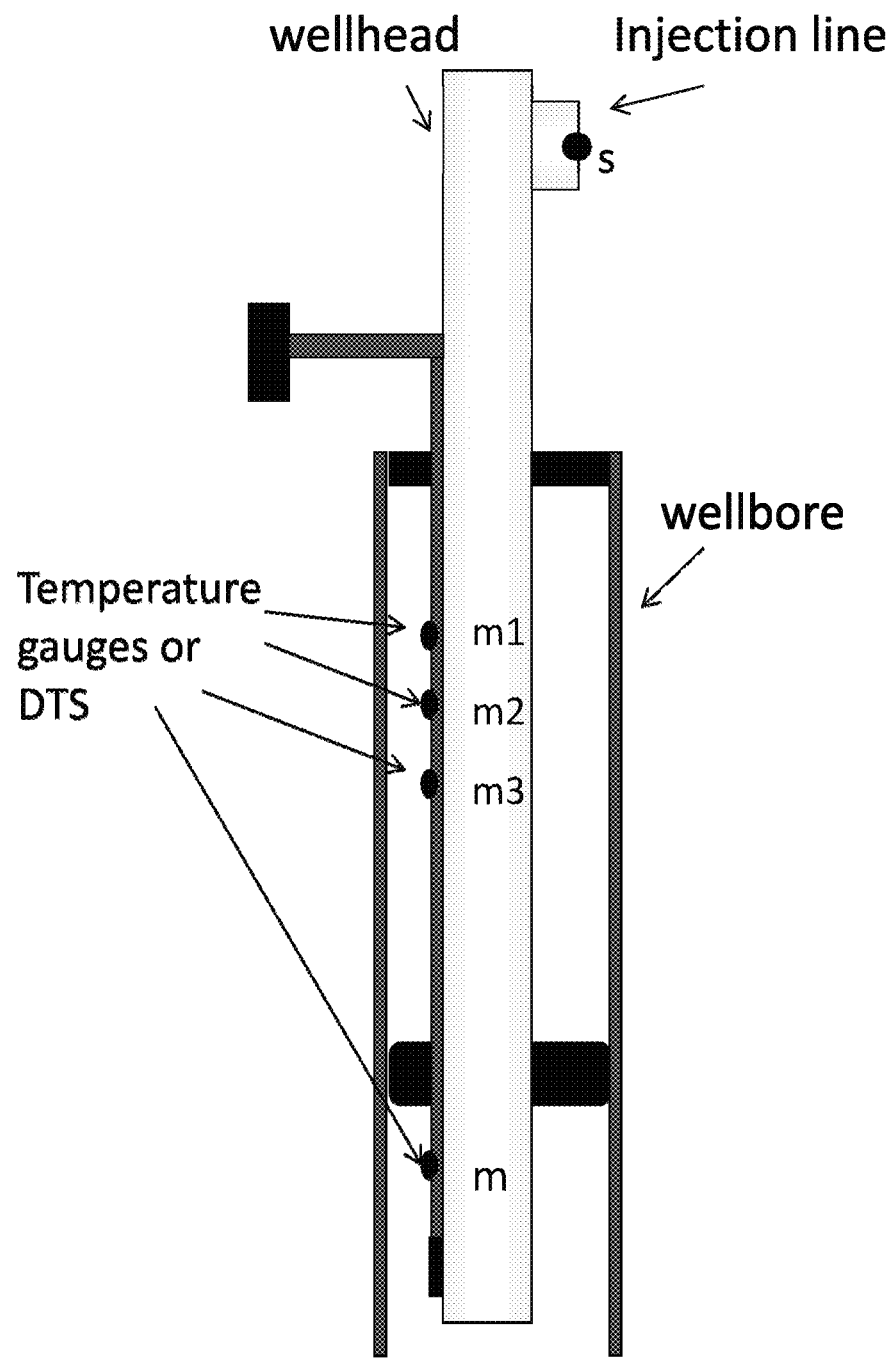

METHOD FOR DETERMINING A STEAM DRYNESS FACTOR

The present invention relates to methods for determining steam dryness in a thermal recovery of high-viscosity oil.

Well bottom zone steam treatment is widely used in the oil industry for stimulating high-viscosity oil production. The traditional method of steam stimulation provides for injecting the calculated volume of a coolant through the injection wells. Usually the 0.7-0.8-dry saturated steam is used as a coolant. The steam dryness is one of the critical parameters of thermal methods of the heavy oil recovery that are based on the injection of steam to the reservoir. When steam flows down from the surface to the perforation depth, a portion of the steam is condensed into water due to heat exchange with the surrounding rock. In case of deep reservoir beds, or insufficient thermal well insulation, or low injection rates etc., the steam can completely be condensed to hot water. This leads to breakdown in process of thermal recovery (steamflooding, steam well treatment) and reduce efficiency thereof due to rapid internal energy loss when steam condensed.

The known prior art methods for downhole steam dryness determination are based on a well steam sampling, the use of complex measurement devices or expensive chemical agents as tracers.

Thus, for example, U.S. Pat. No. 5,470,749, 1995, describes a method for controlling steam dryness wherein the well steam is sampled and mixed with a small amount of the surface active agent; RF Patent No 1046665, 1983, describes a method for determining steam dryness comprising measuring static pressure and two check parameters functionally related to steam dryness.

The closest prior art to the invention is a method for determining well steam dryness comprising steam injection and the steam dryness determination at various locations along the well (U.S. Pat. No. 4,581,926 dated Apr. 15, 1986). According to the known method a special device with a rotating element is lowered into a well, the flow rate and density are measured, followed by the steam consumption and the dryness calculation at any location along the well length. The method shortcomings are the necessity to use an additional device and computational complexity.

The invention provides for a simple, applicable in the field method for determining steam dryness directly during thermal treatment of high-viscosity oil reservoirs. It is achieved by adding a non-condensable gas into a saturated steam being injected into a well, and determining the steam dryness at the various locations along the well by the following formula:

$$Q_m = Q_s \cdot \frac{z_{gas,m}}{z_{gas,s}} \cdot \frac{z_{steam,s}}{z_{steam,m}} \cdot \frac{P_{steam,m}}{P_{steam,s}} \cdot \frac{P_s - P_{steam,s}}{P_m - P_{steam,m}}$$

where,
$Q_s$ is the wellhead steam dryness,
$P_s$ is the wellhead injection pressure,
$P_m$ is the total system pressure at any location (m) within the wellbore,
$P_{steam,s}$ is the partial steam pressure at the condensation temperature $T_s$ in the wellhead,
$P_{steam,m}$ is the partial steam pressure at the condensation temperature $T_m$ at the location (m) within the wellbore,
z is the steam and non-condensable gas compressibility in the wellhead and at the location (m) in the wellbore.

The total and partial pressures $P_m$, $P_{steam,s}$ and $P_{steam,m}$ are determined by temperatures $T_s$ and $T_m$ measured at the wellhead and at the location (m) before and after adding of non-condensable gas.

The content of the non-condensable gas is no more than 30% of total steam-gas mixture.

Adding of up to 30% of the non-condensable gas provides for a noticeable temperature fall from 30° up to 50° which can be used in calculations. Addition of more amount of non-condensable gas is inappropriate from economic and technical point of view (due to possible substantial decrease in temperature).

As non-condensable gases, hydrocarbon gases can be used such as methane, ethane, propane, butane etc. which are non-condensable under the present operation conditions, and also nitrogen, carbon dioxide etc.

The proposed method for determining steam dryness is based on the fact that the introducing of non-condensable gas changes partial steam pressure. Correspondingly the steam condensation temperature also changes. Therefore, the borehole temperature or pressure measurements can be used to evaluate the steam dryness. According to the Dalton's law the partial pressure of a component $p_j$ is equal to the mole fraction of this component in gas $y_j$ times the total pressure of the system p:

$$p_j = y_j p \tag{1}$$

Therefore, adding of a non-condensable gas to the steam being injected leads to reducing of the partial steam pressure (total injection pressure remains the same). Due to the constant heat losses from the wellbore to surrounding rocks, the steam will condense to water along the whole well length. As the steam dryness decreases, the mole fraction of the steam in a gas phase $y_{steam}$ steam will be reduced too. This, in its turn, leads to changing of the partial steam pressure (as to (1)) and corresponding reduction in the steam condensation temperature.

Thus, knowing the wellhead steam dryness, its pressure and temperature, it is possible to determine the steam dryness along the whole well based on measured pressure and temperature. According to the Dalton's law (1) and equation of state for real gases $$\frac{P_s}{z_{steam,s} \frac{w_{steam,s}}{\mu_{steam}} + z_{gas,s} \frac{w_{gas}}{\mu_{gas}}} = \frac{P_{steam,s}}{z_{steam,s} \frac{w_{steam,s}}{\mu_{steam}}} \tag{2}$$

where,
$P_s$ is the wellhead injection pressure, $P_{steam,s}$ is the partial steam pressure at the condensation temperature $T_s$ in the wellhead, w,μ,z are the mass flow rate, molecular weight, and the steam and non-condensable gas compressibility respectively.

Therefore, steam and water mass flow rates are as follows;

$$w_{steam,s} = \frac{P_{steam,s} \cdot \left(z_{gas,s} \frac{w_{gas}}{\mu_{gas}}\right)}{(P_s - P_{steam,s}) \cdot \left(z_{steam,s} \frac{1}{\mu_{steam}}\right)} \tag{3}$$

$$w_{water,s} = \frac{(1 - Q_s) \cdot w_{steam,s}}{Q_s} \tag{4}$$

where, $Q_s$ is the known wellhead steam dryness.

The above relationships are also valid for any location (m) along the wellbore, where $P_m$ is the total system pressure at the location (m) (at the given depth), and $P_{steam,m}$ is the partial steam pressure at the condensed temperature $T_m$ at the location (m). From a material balance equation and the use of a non-condensable gas, the steam dryness at any location (m) within the wellbore is determined:

$$Q_m = Q_s \cdot \frac{z_{gas,m}}{z_{gas,s}} \cdot \frac{z_{steam,s}}{z_{steam,m}} \cdot \frac{P_{steam,m}}{P_{steam,s}} \cdot \frac{P_s - P_{steam,s}}{P_m - P_{steam,m}} \quad (5)$$

The method should be implemented as follows:

In process of thermal high viscosity oil reservoir stimulation, the $Q_s$=95%-dry steam is injected into the well.

The wellhead pressure and temperature are $P_s$=70 atm and $T_s$=287.7° C., respectively, the bottom-hole ones will be $P_m$=60 atm and $T_m$=277.5° C., respectively.

After adding of a non-condensable gas (methane) in amount of 20% of total steam-gas mixture mass the wellhead and the bottom-hole temperature measurements showed as follows:

a) the wellhead temperature $T_s$ decreases down to 273° C.,
b) the bottom-hole temperature $T_s$ decreases down to 251° C.

Water-phase diagrams (P-T) have provided corresponding partial pressures such as, $P_{steam,s}$=56 atm and $P_{steam,m}$=39 atm.

Using an assumption that the gases are ideal (z=1) and substituting to formula (5), we obtain as follows:

$Q_m$=0.44

Therefore, the bottom-hole steam dryness constitutes 44%.

A certain advantage of the proposed method is its simplicity for field application. There is no need in mounting additional downhole measuring equipment. Temperature measurements can be made both by using distributed temperature measurement systems and by standard temperature logging.

The invention claimed is:

1. A method for determining saturated steam dryness in a well comprising:
   injecting steam having a known wellhead steam dryness $Q_s$ into the well at a wellhead injection pressure $P_s$,
   determining a total system pressure $P_m$ at any selected location (m) within a wellbore of the well,
   adding a non-condensable gas into the steam being injected,
   determining a partial steam pressure $P_{steam,s}$ at a condensation temperature $T_s$ in a wellhead of the well (s),
   determining a partial steam pressure $P_{steam,m}$ at a condensation temperature $T_m$ at the selected location (m) in the wellbore, and
   determining the steam dryness at the selected location (m) by formula:

$$Q_m = Q_s \cdot \frac{z_{gas,m}}{z_{gas,s}} \cdot \frac{z_{steam,s}}{z_{steam,m}} \cdot \frac{P_{steam,m}}{P_{steam,s}} \cdot \frac{P_s - P_{steam,s}}{P_m - P_{steam,m}}$$

where
   $Q_s$ is the known wellhead steam dryness,
   $P_s$ is the wellhead injection pressure,
   $P_m$ is the total system pressure at the selected location (m) in the wellbore,
   $P_{steam,s}$ is the partial steam pressure at the wellhead (s),
   $P_{steam,m}$ is the partial steam pressure at the selected location (m) in the wellbore,
   $Z_{steam,s}$ is a compressibility of steam in the wellhead (s),
   $Z_{steam,m}$ is a compressibility of steam at the selected location (m) in the wellbore,
   $Z_{gas,s}$ is a compressability of the non-condensable gas in the wellhead (s),
   $Z_{gas,m}$ is a compressability of the non-condensable gas at the selected location (m) in the wellbore.

2. The method according to claim 1, wherein after adding the non-condensable gas, the condensation temperature $T_s$ in the wellhead (s) and condensation temperature $T_m$ at the selected location (m) are measured, and partial steam pressure $P_{steam,s}$ at the wellhead and partial steam pressure $P_{steam,m}$ at the selected location (m) in the wellbore are determined from the measured condensation temperatures $T_s$ and $T_m$.

3. The method according to claim 1, wherein a content of the non-condensable gas is no more than 30% of the total steam-gas mixture.

4. The method according to claim 1 wherein before adding the non-condensable gas a temperature at the selected location (m) in the wellbore is measured and the total system pressure at the selected location (m) in the wellbore is determined from the measured temperature.

5. The method according to claim 1 wherein the non-condensable gas is selected from the group consisting of methane, ethane, propane, butane, nitrogen, carbon dioxide.

* * * * *